(12) United States Patent
Pisano et al.

(10) Patent No.: US 8,829,021 B2
(45) Date of Patent: *Sep. 9, 2014

(54) TREATMENT OF PEDIATRIC TUMORS

(75) Inventors: Claudio Pisano, Aprilia (IT); Loredana Vesci, Rome (IT); Paolo Carminati, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 284 days.

This patent is subject to a terminal disclaimer.

(21) Appl. No.: 12/669,134

(22) PCT Filed: Jul. 3, 2008

(86) PCT No.: PCT/EP2008/058601
§ 371 (c)(1),
(2), (4) Date: Feb. 17, 2010

(87) PCT Pub. No.: WO2009/015981
PCT Pub. Date: Feb. 5, 2009

(65) Prior Publication Data
US 2010/0197718 A1    Aug. 5, 2010

(30) Foreign Application Priority Data
Aug. 1, 2007   (EP) .................................. 07113603

(51) Int. Cl.
*A61K 31/4375*  (2006.01)
*A61P 35/00*    (2006.01)
*C07D 457/14*   (2006.01)
*A61K 31/4745*  (2006.01)

(52) U.S. Cl.
CPC .................................. *A61K 31/4745* (2013.01)
USPC ............................................ 514/283; 546/50

(58) Field of Classification Search
CPC .......................... A61K 31/4745; C07D 457/14
USPC ............................................ 514/283; 546/50
See application file for complete search history.

(56) References Cited

FOREIGN PATENT DOCUMENTS

| EP | 1044977 | 10/2000 |
|---|---|---|
| WO | 2007/071603 A | 6/2007 |
| WO | WO 2008/098701 A | 8/2008 |

OTHER PUBLICATIONS

Shitara, et al., "Irinotecan for children with relapsed solid tumors.", Pediatric Hematology and Oncology, 2006, 23(2):103-110.
Hiroyuki Fujisaki, et al., Chemotherapy on Childhood Tumors Utilizing CPT-11 in the Department, Pediatric Cancer, Nov. 2002, vol. 39, No. 3, p. 447.
Japanese Office Action issued on Jun. 25, 2013.

*Primary Examiner* — Sreeni Padmanabhan
*Assistant Examiner* — Sahar Javanmard
(74) *Attorney, Agent, or Firm* — Lucas & Mercanti, LLP

(57) ABSTRACT

A subclass of camptothecin derivatives is disclosed to be useful for the preparation of a medicament for the treatment of pediatric tumors such as for examplerhabdomyosarcoma, primitive neuroectodermal tumors (PNET) and neuroblastoma.

5 Claims, No Drawings

TREATMENT OF PEDIATRIC TUMORS

CROSS-REFERENCE TO RELATED APPLICATIONS

This application is a 371 of PCT/EP2008/058601 filed on Jul. 3, 2008, which claims the benefit of European Patent Application No. 07113603.0 filed on Aug. 1, 2007, the contents of each of which are incorporated herein by reference.

FIELD OF THE INVENTION

The present invention relates to the use of a subclass of camptothecin derivatives for the preparation of a medicament for the treatment of pediatric tumors such as, for example, rhabdomyosarcoma, primitive neuroectodermal tumors (PNET) and neuroblastoma.

BACKGROUND OF THE INVENTION

Camptothecin derivatives are DNA-topoisomerase I inhibitors that have emerged as a prominent class of anticancer agents. Together with the taxanes, the topoisomerase I inhibitors are presumably the most important new class of anticancer drugs introduced into clinical practice. Pre-clinical studies demonstrated significant in vitro and in vivo activity of topoisomerase I inhibitors, such as camptothecin and its derivatives, on a broad range of tumors. The results from clinical trials were promising, as shown by the registration of two topoisomerase inhibitors, topotecan and irinotecan (also known as CPT-11), in many European countries and in the USA, for treatment of patients with ovarian and colorectal cancer, respectively. Other derivatives are currently at different stages of clinical development.

In patent application EP1044977 and in J. Med. Chem. 2001, 44, 3264-3274, camptothecin derivatives are described which bear an alkyloxime O-substituted at position 7 and which are endowed with antitumor activity higher than the compound of reference topotecan. Moreover these camptothecin derivatives bearing an imino group on position 7, also show an improved therapeutic index. Among these compounds one of the preferred molecules was shown to be 7-t-butoxyiminomethylcamptothecin (CPT 184, also known as ST1481 or gimatecan).

Although the annual mortality rate of pediatric cancer has decreased over the past two decades, the proportion of deaths from tumors of the central nervous system in the same population has increased from 18 percent to 30 percent. The cause of childhood brain tumors is largely unknown. While radiation exposure is a recognized risk factor for brain tumors, the role of other environmental toxins is unclear in children. Less than 5 percent of pediatric brain tumors are associated with a known genetic disease, such as neurofibromatosis, a common genetic condition associated with benign tumor growths on nerve tissue (Serletis D, Parkin P, Bouffet E, Shroff M, Drake J M, Rutka J T *J Neurosurg.* 2007 106: 363-7).

Although only 1 percent of childhood brain tumors are detected at birth or in the first few months of life, a significant number are diagnosed before age five, suggesting a developmental defect. As a matter of fact, defects in developmental growth signaling pathways have recently been identified in embryonal tumors.

Historically, a diagnosis of brain cancer is provided by a pathologist, who views tissue samples under a microscope. Upon visual inspection of brain cells (histology), pathologists can then classify the tumor type (Miller C R, Perry A *Arch Pathol Lab Med.* 2007 131: 397-406). The limitations of this practice are that many brain tumors have a similar histology when they are actually very different tumors with greatly different prognoses and responses to therapies. There are some children diagnosed with medulloblastoma who respond well to therapy while others do not. Therefore, tumor classification is moving toward the use of molecular signatures to more precisely classify and grade tumor tissues (Sardi I Cavalieri D, Massimino M *Paediatr Drugs.* 2007 9:81-96).

In addition to confusing tumor classifications, in the past, pediatric tumors were considered to be similar to tumors in adults. However, recent studies have revealed that pediatric brain tumors are very different biologically than their adult counterparts. One example is a tumor called fibrillary astrocytoma, a tumor that occurs both in children and adults (Collins *Nat Clin Pract Oncol.* 2007 4: 362-74).

Biologically they behave very differently even though they look the same under the microscope. This disease in children rarely will become a high-grade tumor during childhood years, but in adults it can turn into higher grade tumors.

These observations are further supported by recent studies of molecular markers. Mutations in specific genes that cause disease in adults may not be the cause of disease in children. Future studies should provide fertile opportunities for drug target discoveries and related molecularly targeted therapies.

The use of surgery in treatment of pediatric brain tumors is well-established, but more effective treatments are needed. Imaging technologies have been used to non-invasively assess tumor status and treatment in children, thus eliminating the need to obtain repeated biopsies of the same tumor. The gains achieved in improved surgical resection of brain tumors also can be attributed to improved imaging technologies (Khatua S, Jalali R *Pediatr Hematol Oncol.* 2005 22: 361-71). Surgeons are now better able to locate a tumor and assess the margins, removing less of the normal brain tissue. This is a significant improvement because there is a direct correlation between the extent of tumor resection and survival in some types of brain tumors in pediatric patients. Improved imaging technologies have also spurred advances in radiation therapy techniques (Greco C Wolden S. *Cancer.* 2007 109: 1227-38). In addition to providing information about the size and location of a tumor, imaging techniques are also providing data to evaluate the biochemical profile of the tumor, as well. Studies have shown that changes in the ratio of certain biochemical components of a tumor can aid an oncologist in determining if a tumor is actively growing (Chen L, Madura K. *Cancer Res.* 2005 65:5599-606; Chung T D, Broaddus W C *Mol Interv.* 2005 5:15-9). These results would support the choice of aggressive or less stringent treatment regiments.

Blood flow to tumors and tissues in the brain is also being examined through imaging. Evaluation of changes in the amount of blood flowing to tissues in the brain is essential to assess the effectiveness of anti-angiogenic drugs. These drugs do not target the tumor directly, but attack the cells lining the blood vessels that support tumor growth. The tumor size may not shrink, but a decrease in the number of blood vessels surrounding the tumor is a significant advance (Kieran M W *J Neurooncol.* 2005 75: 327-34; Kibble A. *IDrugs.* 2007 10: 5-7). Anti-angiogenic drugs will most likely be combined with other agents that target the tumor directly. Currently, these agents are being tested alone for safety.

Neuroblastoma is one of the most common extracranial solid tumours in childhood with a poor prognosis in its advanced stage. Treatment failure is often associated to the occurrence of drug resistance. To date, treatment of pediatric neuroblastoma is still dismal, and therefore novel effective drugs are awaited. (Gutierrez J C, Fischer A C, Sola J E, Perez E A, Koniaris L G *Pediatr Surg Int.* 2007 23: 637-46). Rhabdomyosarcoma is the most common soft-tissue sarcoma of childhood, representing 5% of all childhood cancers (M. Beth McCarville, Sheri L. Spunt and Alberto S. Pappo *AJR* 2001; 176:1563-1569). It is thought to arise from primitive mesenchymal cells committed to skeletal muscle differentiation and can occur in a variety of organs and tissues, including those that lack striated muscle.

Primitive neuroectodermal tumors (PNETs) develop from primitive or undifferentiated neuroepithelial cells from the early development of the nervous system. PNET of the posterior fossa, or medulloblastoma, is the most common brain tumor in children. In 80% of cases, patients with PNETs develop acute hydrocephalus accompanied by severe symptoms of headache and vomiting, and they require urgent resection of the mass (de Bont J M, den Boer M L, Kros J M, Passier M M, Reddingius R E, Smitt P A, Luider T M, Pieters R. *J Neuropathol Exp Neurol.* 2007 66: 505-516).

DESCRIPTION OF THE INVENTION

It has now surprisingly found that two camptothecin derivatives have shown a superior efficacy with respect to the reference compound (irinotecan) in terms of tumor volume inhibition (TVI %), against a wide spectrum of pediatric tumors xenografts in vivo. Moreover, the treatment was generally well tolerated by the animals, with no signs of acute or delayed toxicity.

In particular the main object of the present invention is the use of a compound of Formula I,

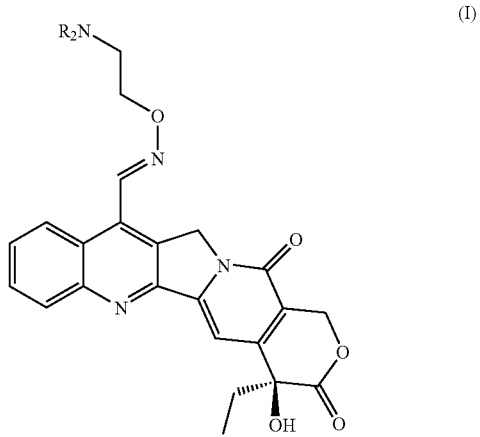

(I)

where R is hydrogen or $C_1$-$C_4$ alkyl,
for the preparation of a medicament for the treatment of pediatric tumors such as, for example, rhabdomyosarcoma, primitive neuroectodermal tumors (PNET) and neuroblastoma.

Compounds of Formula (I) also comprise tautomers, geometrical isomers, optically active forms as enantiomers, diastereomers and racemate forms, as well as pharmaceutically acceptable salts of the compounds of Formula (I).

Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

Preferably R is hydrogen or methyl.

Preferred compounds of Formula (I) are:
7-(2-amino)ethoxyiminomethylcamptothecin, (ST1968, also known as CPT188) and 7-(2-dimethylamino)ethoxyiminomethylcamptothecin (ST1969).

The compounds of Formula (I) may be prepared from readily available starting materials using the following general methods and procedures. It will be appreciated that where typical or preferred experimental conditions (i.e. reaction temperatures, time, moles of reagents, solvents, etc.) are given, other experimental conditions can also be used, unless otherwise stated. Optimum reaction conditions may vary with the particular reactants or solvents used, but such conditions can be determined by one skilled in the art by routine optimisation procedures. Specific reference is made to the methods described in patent application EP1044977 and in J. Med. Chem. 2001, 44, 3264-3274.

A method of treating a patient suffering from tumor pathology selected from the group consisting of rhabdomyosarcoma, primitive neuroectodermal tumors (PNET) and neuroblastoma comprising administering a therapeutically effective amount of a compound of Formula (I) as described above represents one of the aspects of the present invention.

The term "therapeutically effective amount" as used herein refers to an amount of a therapeutic agent needed to treat, ameliorate a targeted disease or condition, or to exhibit a detectable therapeutic effect.

For any compound, the therapeutically effective dose can be estimated initially either in cell culture assays, for example, of neoplastic cells, or in animal models, usually mice or rats.

The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 100 mg/kg, preferably 0.05 mg/kg to 50 mg/kg. Compositions may be administered individually to a patient or may be administered in combination with other agents, drugs or hormones.

The medicament may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N. J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human pediatric subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal, rectal means or locally on the diseased tissue after surgical operation.

Dosage treatment may be a single dose schedule or a multiple dose schedule.

The invention will now be illustrated in greater detail by means of non-limiting Examples.

EXAMPLES

In Vivo Antitumoral Activity on Different Pediatric Tumor Xenograft Models

The antitumor effect was evaluated against different human pediatric tumor models: SK-ND-AS (neuroblastoma); PSFK (primitive neuroectodermal tumors/PNET); TE-671 (rhabdomyosarcoma). ST 1968 was evaluated in comparison to CPT-11 (irinotecan) by intravenously delivery of 30 mg/10 ml/kg for ST1968 and 50 mg/10 ml/kg for CPT-11 according to the schedule q4dx4.

Methods

Exponentially growing tumor cells were injected s.c. into nude athymic mice. The number of tumor cells was previously chosen by a growth curve. Mice were housed inside cages of makrolon (33.2×15×13 cm) with stainless steel cover-feed and sterilized and dust-free bedding cobs. Animals were housed under a light-dark cycle, keeping temperature and humidity constant. Parameters of the animal rooms were assessed as follows: 22±2° C. temperature, 55±10% relative humidity, about 15-20 filtered air changes/hour and 12 hour circadian cycle of artificial light (7 a.m., 7 p.m.). At request, the environmental conditions were monitored and the data are retained in Animal Housing Archives. Drinking water was supplied ad libitum. Each mouse was offered daily a complete pellet diet (GLP 4RF21, Mucedola) throughout the study. The analytical certificates of animal food and water are retained at Sigma-Tau premises. All animals were weighed before starting the experiment and were subdivided into the different dosage groups.

Each cage was identified by a paper tag indicating: cage number, group, date of tumor injection, starting date of treatment, name of the test item, dose and route of administration, date of sacrifice.

Tumor growth was followed by biweekly measurements of tumor diameters with a Vernier caliper. Tumor volume (TV, mm$^3$) was calculated as: [length (mm)×width (mm)$^2$]/2, where the width and the length are the shortest and the longest diameters of each tumor, respectively.

The efficacy of the drug treatment was assessed as tumor volume inhibition (TVI %) in treated versus control mice, calculated as: 100−[(mean tumor volume of treated animals/mean tumor volume of control animals)×100].

The toxicity of the drug treatments was determined as: body weight loss percent (% BWL max)=100−(mean $BW_{day\ x}$/mean $BW_{day\ 1}$×100), where $BW_x$ is the mean BW at the day of maximal loss during the treatment and $BW_1$ is the mean BW on the 1$^{st}$ day of treatment.

Results

In the in vivo studies, ST1968 showed a remarkable antitumor activity with an appreciable rate of complete tumor regressions in all models compared with CPT-11. The most impressive antitumor effects were observed against PNET and rabdomiosarcoma models, as documented by the high rate of complete responses: the tumor volume inhibition (TWI) was 99% or 100% respectively (Table 1). Interestingly, ST1968 treatment was generally well tolerated by mice with no signs of acute or delayed toxicity.

TABLE 1

Antitumor activity of ST1968 on human pediatric tumor xenograft models

| Tumor | Line | Compound | Dose (mg/kg) | Method of administ. | TVI % |
|---|---|---|---|---|---|
| Rhabdo myosarcoma | TE-671 | ST1968 | 30 | q4dx4 | 99 |
|  |  | irinotecan | 50 | q4dx4 | 73 |
| Primitive neuroectodermal tumors (PNET) | PFSK | ST1968 | 30 | q4dx4 | 100 |
|  |  | irinotecan | 50 | q4dx4 | 95 |
| Neuroblastoma | SK-N-AS | ST1968 | 30 | q4dx4 | 98 |
|  |  | irinotecan | 50 | q4dx4 | 91 |

The invention claimed is:

1. Method of treating a mammal suffering from a pediatric tumor pathology selected from the group consisting of rhabdomyosarcoma, primitive neuroectodermal tumors (PNET) and neuroblastoma comprising administering a therapeutically effective amount of a compound of Formula I,

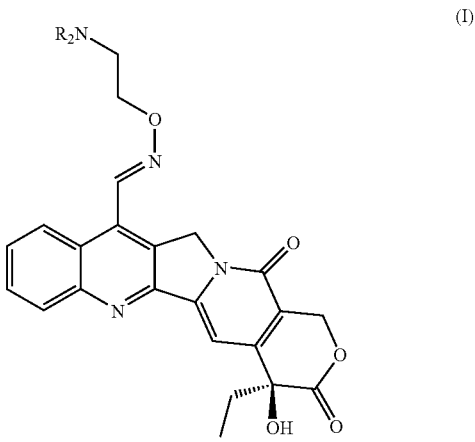

where R is hydrogen or methyl, or a pharmaceutical composition containing the same and pharmaceutically acceptable carriers and/or excipients.

2. The method according to claim 1, wherein the pediatric tumors are head and neck carcinoma selected from the group consisting of rhabdomyosarcoma, primitive neuroectodermal tumors (PNET) and neuroblastoma.

3. The method of claim 1, wherein the compound of Formula I is
7-(2-amino)ethoxyiminomethylcamptothecin or
7-(2-dimethylamino)ethoxyiminomethylcamptothecin.

4. The method of claim 1, wherein the therapeutically effective amount is from 0.01 mg/kg to 100 mg/kg.

5. The method of claim 1, wherein the therapeutically effective amount is from 0.05 mg/kg to 50 mg/kg.

* * * * *